US007559926B1

(12) United States Patent
Blischak

(10) Patent No.: US 7,559,926 B1
(45) Date of Patent: Jul. 14, 2009

(54) ACTUATION SYSTEM AND METHOD FOR AN IMPLANTABLE INFUSION PUMP

(75) Inventor: Brian Blischak, Allen, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 908 days.

(21) Appl. No.: 10/755,985

(22) Filed: Jan. 13, 2004

Related U.S. Application Data

(60) Provisional application No. 60/439,780, filed on Jan. 13, 2003, provisional application No. 60/439,909, filed on Jan. 14, 2003.

(51) Int. Cl.
*A61K 9/22* (2006.01)

(52) U.S. Cl. ................................ 604/891.1; 604/890.1

(58) Field of Classification Search ................ 604/503, 604/502, 71, 131, 82, 132–133, 140, 142, 604/288.01–288.04, 890.1, 891.1
See application file for complete search history.

(56) References Cited

U.S. PATENT DOCUMENTS 4,193,397 A * 3/1980 Tucker et al. ............... 604/502
4,405,305 A * 9/1983 Stephen et al. .............. 604/502
4,552,561 A * 11/1985 Eckenhoff et al. ....... 604/891.1
4,604,090 A * 8/1986 Reinicke ..................... 604/118
4,772,263 A 9/1988 Dorman et al.
4,813,951 A * 3/1989 Cannon ................... 604/891.1
5,053,031 A * 10/1991 Borsanyi ................. 604/891.1
5,387,192 A * 2/1995 Glantz et al. ........... 604/288.02
5,700,245 A * 12/1997 Sancoff et al. .............. 604/145
5,976,109 A 11/1999 Heruth
6,635,049 B1 10/2003 Robinson et al.
6,736,795 B2 * 5/2004 Michel ....................... 604/131
2004/0065615 A1 * 4/2004 Hooper et al. .............. 210/650
2004/0143217 A1 * 7/2004 Michel ....................... 604/131

* cited by examiner

*Primary Examiner*—Nicholas D Lucchesi
*Assistant Examiner*—Aarti Bhatia
(74) *Attorney, Agent, or Firm*—Christopher S. L. Crawford; Peter Lando; Melissa Acosta

(57) ABSTRACT

The invention relates to an actuation system and method for an implantable infusion pump. In an example, a working fluid is placed in an actuator. Upon actuation, the working fluid is driven into a piston cylinder. Upon deactuation, the actuator draws the fluid from the cylinder through a restrictor at a rate dictated by the motivating force, fluid viscosity, and restriction. Driving of the piston may produce a bolus dosage or fill a supplemental flow chamber for subsequent delivery. The exemplary system may be configured by selecting a fluid volume and a viscosity. These, in combination, produce a prescribed fluid delivery rate (or recharge rate) and cumulative flow volume provided to a patient over a time period or in a bolus dose. The system may also be configured to limit the total dosage of a bolus injection, or the rate of a supplemental dosage. In this manner, the system is safe, preventing overdose.

4 Claims, 3 Drawing Sheets

30
32
34
36
38
40
42
44
46
48
49
50

ACTUATION SYSTEM AND METHOD FOR AN IMPLANTABLE INFUSION PUMP

CROSS-REFERENCE TO RELATED APPLICATIONS

Priority is hereby claimed to U.S. Provisional Application No. 60/439,780, filed Jan. 13, 2003 and U.S. Provisional Application No. 60/439,909, filed Jan. 14, 2003, the disclosures of which are hereby incorporated herein by reference. The present application is related to the co-pending and commonly assigned U.S. patent application Ser. No. 10/756,673, titled "Multi-Stable Valves for Medical Applications and Methods for Use Thereof," filed concurrently herewith, the disclosure of which is hereby incorporated herein by reference.

TECHNICAL FIELD

The invention in general relates to implantable infusion pumps. More specifically, the invention relates to actuation systems and methods for delivering supplemental drug dosages in continuous or bolus patterns from an implantable infusion system.

BACKGROUND OF THE INVENTION

Implantable drug infusion therapy has been used to treat various ailments including pain, spasticity, and cancer. These drug pumps and delivery systems have been used to deliver pain medication, anti-spasmatic agents, chemotherapeutic agents, and other pharmaceutical agents. For example, intraspinal drug delivery may be used to treat chronic pain. By utilizing these systems, pharmaceutical agents may be delivered in relatively lower doses to a specific region of treatment. In this manner, full body dilution and membrane barriers may be bypassed.

Implantable drug delivery systems have several advantages over external drug pumps, oral medications, suppositories, and injections. These implantable systems may be less obtrusive, encumbering, and may deliver smaller doses to targeted regions. Pills, suppositories, and injections usually deliver large doses of pharmaceutical agents that pass through a larger portion of the body to reach the treatment area. The large dilution ratio caused by this passing requires a large dose to achieve an effective concentration in the treatment area. In addition, patients must remember to administer the correct dose at the appropriate time to achieve the desired therapeutic levels when using pills, suppositories, and injections.

While external infusion pumps overcome some of the limitations of pills, injections, and suppositories, they are often cumbersome and inconvenient. These devices must typically be worn or strapped to the patient, encumbering clothing selection, participation in activities such as bathing or swimming, and there is often a risk of damage to the external pump. In addition, catheter incision points are subject to infection.

However, current versions of implantable infusion pump systems also have disadvantages. Typically, implantable infusion pump systems provide limited patient control and safety features. Many systems are limited to a single flow rate preprogrammed by a doctor. In these systems, patients lack control of the system for responding to events. In the case of pain management, patients may experience an event of increased pain during certain parts of the day or after exertion. However, with the present systems that have minimal or no control, the patient has no means of adjusting dosage rates to compensate for these or other events of pain increase.

An example of an infusion pump providing limited patient control is the pump described in U.S. Pat. No. 4,772,263, the disclosure of which is hereby incorporated herein by reference. Such a pump is an implantable infusion pump which attempts to approximate a uniform pressure difference between a drug chamber and an internal body pressure, thereby delivering a more predictable flow of drug to a treatment site despite changes in temperature or barometric pressure. The particular pump uses a balloon-like structure to apply a pressure to a drug solution contained therein. Pumps such as the one described in U.S. Pat. No. 4,772,263, which maintain a uniform pressure difference despite changes in temperature and ambient pressure are sometimes referred to as "constant flow pumps." Constant flow pumps may or may not include an electrical motor and may use means other than a balloon-like structure to apply pressure to a drug solution.

In certain devices which provide patients with limited control, the systems often lack sufficient features to prevent overdose. For example, if a pain patient is given the ability to implement a bolus dose, that patient may implement more than one bolus dose during pain. Often, a lag time exists between the implementation of the bolus and the patient's perception of its effects. As a result, a patient may attempt to implement a second, third or fourth bolus dose, leading to an overdose situation.

As such, many infusion pump systems suffer from deficiencies in providing adequate patient control and safety measures to prevent overdosing by the patient. Many other problems and disadvantages of the prior art will become apparent to one skilled in the art after comparing such prior art with the present invention as described herein.

BRIEF SUMMARY OF THE INVENTION

Embodiments of the present invention comprise an actuation system. In an exemplary embodiment, an actuator is connected to a working fluid reservoir through a transmission line and restriction. Filling and/or contracting of the working fluid reservoir may result in corresponding actions on a pharmaceutical fluid reservoir to administer a dose to a treatment site. Such an embodiment may provide such dosages as a bolus dosage or a supplemental continuous flow dosage, among others. Some embodiments may further include a working fluid that is transferred from an actuator to a fluid reservoir through a restriction, upon activation of the actuator. The actuator can then draw the working fluid back from the fluid reservoir through the restrictor at a rate in accordance with the viscosity of the working fluid.

Some embodiments may include an actuator system situated in a drug infusion system such that actuation and filling of the first reservoir causes the filling of a second reservoir. After actuation, a gradual emptying of the first fluid reservoir causes a gradual emptying of the second fluid reservoir, resulting in a supplemental flow rate added to a basal dosage rate.

In another embodiment, an actuation system may behave such that actuation causes the filling of the first fluid reservoir and emptying of the second fluid reservoir. Accordingly, deactuation results in a drainage of the first fluid reservoir and gradual filling of the second fluid reservoir. This embodiment provides, among other things, a bolus injection and gradual draw from a basal dosage rate.

Further aspects of the invention comprise a method for using an actuation system. An embodiment may include actuating an actuator, filling a first fluid reservoir and, upon deactuation, drawing fluid from the fluid reservoir. An actuation system may be configured such that the actuation and filling steps cause the injection of a bolus dosage, and the draw down causes the gradual refilling of a bolus reservoir. The refilling may draw from a basal dosage flow. A system may also be configured such that the actuation and filling of the first fluid reservoir causes a filling of a second fluid reservoir, and the deactuation causes a gradual supplemental flow rate to be added to the basal flow rate.

Another embodiment includes a method for establishing dosage rates of control. Such a method may comprise selecting a volume and selecting a flow resistance which result in the implementation of a prescription or desired dosage rate. A device may then be configured with the selected volumes and resistances to provide for supplemental flow and/or bolus flow in accordance with a prescription. A flow resistance may be associated with a selected viscosity or viscous fluid. Alternately, a resistance may be from a selected flow restrictor, a flow restrictor setting, or pressure regulator setting.

As such, systems and methods for delivering infused drugs are described. Other aspects, advantages and novel features of the present invention will become apparent from the detailed description of the invention when considered in conjunction with the accompanying drawings.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Patient control of dosing permits adaptation of treatment to events and progressing conditions. In various cases, the safe addition of bolus or supplemental dosing features aids in management of treatment and reduces the consequences of inappropriate dosing. Safe administration of a bolus within prescribed limits permits patients to compensate for unusual events or conditions while preventing overdose. Similarly, safe administration of supplemental doses permits the patient to adapt treatment to routines or to heterogeneous or circadian conditions.

Figure 1:
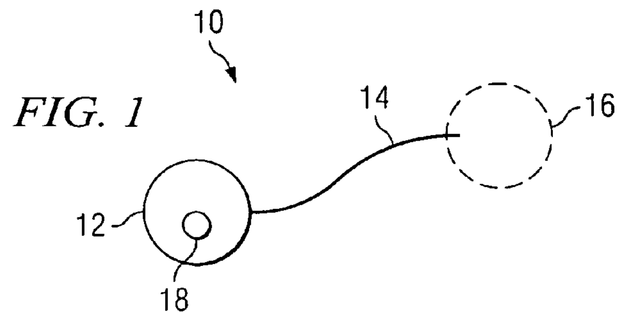
FIG. 1 is a schematic diagram depicting an exemplary application.

FIG. 1 is a schematic diagram of an exemplary embodiment. The delivery system 10 includes an implantable infusion system 12 which delivers a pharmaceutical solution through a catheter 14 to a treatment location 16. The implantable infusion system 12 includes an actuation system 18, which functions to augment flow through catheter 14 upon activation by a patient. Depending upon its purpose, actuator 18 may be located at various points along a flow path from a pharmaceutical solution reservoir, through filters and restrictions, to catheter 14.

The actuator system 18 may function to provide bolus or supplemental flow augmentation. The actuator system 18 may include an actuator, a flow restrictor, and one or more fluid reservoirs. The actuator may be physically accessible by a patient for manipulation or may be remotely controlled, such as through the use of magnetic coupling, capacitive coupling, radio frequency links, or the like. Additionally or alternatively, the actuator may be an electromechanical device.

In one exemplary embodiment, the actuator system 18 may include an actuator, a flow restrictor, and a first and second reservoir. Upon actuation, the actuator may drive fluid into the first reservoir. Subsequently, the actuator may draw the fluid back through the restrictor from the first reservoir at a rate dictated by the drawing force, the size of the restrictor, and the viscosity of the fluid. The first reservoir may be mechanically coupled to a second reservoir such that a bolus dose is implemented upon actuation. In an alternate embodiment, the system may be configured to deliver a supplemental dose as fluid is drawn from the first reservoir. It may be possible for a physician to dictate the rate and volume of doses by manipulating one or more of the driving force, restrictor size, fluid volume, or fluid viscosity.

Figure 2A:
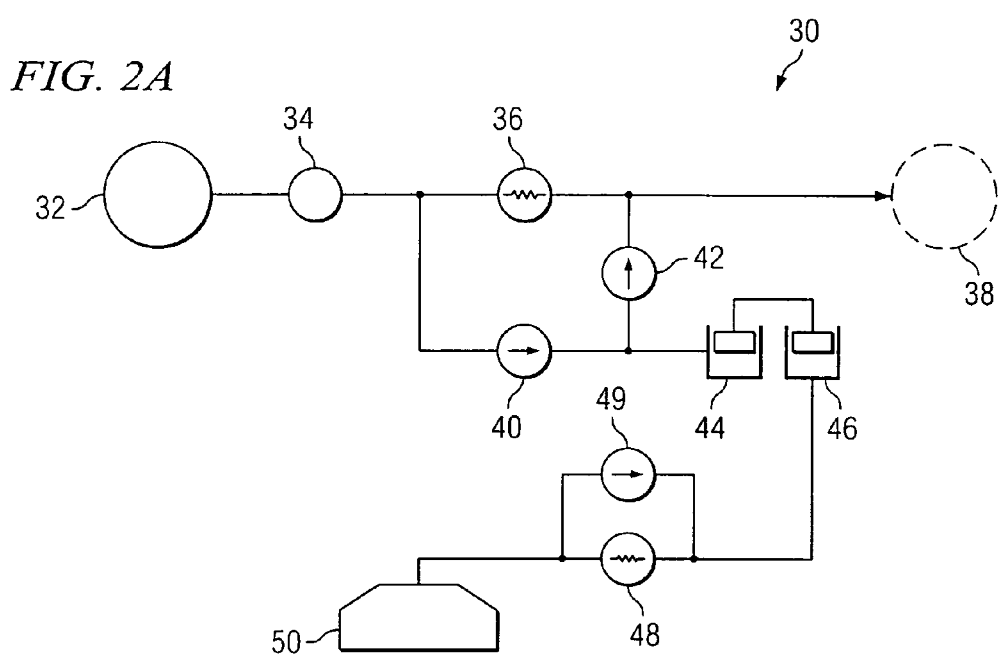
FIG. 2 A is a schematic diagram depicting an exemplary embodiment of the invention.
FIG. 2B is a graph of dosage rates associated with the exemplary embodiment of FIG. 2A.

FIG. 2A represents an exemplary configuration for providing a supplemental flow. The system 30 includes reservoir 32 of a pharmaceutical solution. The reservoir 32 has an associated flow control mechanism which may be driven by pressure, a peristaltic mechanism, osmotic pressure, or any of a number of other methods known in the art. In this illustration the flow control mechanism is flow restrictor 36 positioned downstream of substantially constant pressure reservoir 32. As a result, fluid flows through filter 34 and flow restrictor 36 to the treatment area 38. Flow restrictor 36 and an associated pressure source are selected to provide the desired dosage rate. Alternately, a variable rate pump may be associated with reservoir 32 or placed along the line to provide fluid flow. In an embodiment, a pump associated with reservoir 32 is a constant flow pump including a balloon-like structure which applies a pressure to the fluid therein. Such a constant flow pump may require no electrical power supply or motor to operate.

Actuator 50 is connected through flow restrictor 48 to fluid reservoir 46. In this exemplary embodiment, reservoir 46 is depicted as a piston cylinder. Fluid reservoir 46 is physically connected to fluid reservoir 44 such that an action on fluid reservoir 46 results in a corresponding action on fluid reservoir 44. In this depiction, fluid reservoirs 44 and 46 are shown as piston cylinders. However, various membrane and/or piston systems, as well as other fluid reservoir and handling systems providing operation as described herein, may be used to provide similar functionality.

Actuator 50 may take the form of a mechanical or electrically activated actuator that physically compresses, expelling fluid upon actuation and draws fluid back upon deactuation. The actuator may also be physically manipulated by a patient. For example, the actuator may take the form of a compressible button or bulb, such that a patient may manually apply a pressure to actuator 50, thereby forcing a fluid from the actuator. Alternative embodiments may include other methods of activation, including a combination of activation methods.

When actuator 50 is compressed, fluid is pushed into fluid reservoir 46. Fluid may or may not pass also through a restrictor, such as flow restrictor 48 of the illustrated embodiments. In this embodiment, one-way check valve 49 allows fluid to bypass flow restrictor 48 on its way to fluid reservoir 46, but the fluid must pass through flow restrictor 48 on its way to actuator 50 from fluid reservoir 46. Allowing fluid to bypass flow restrictor 48 on its way to fluid reservoir 46 facilitates a more rapid filling of fluid reservoir 46 than is possible through flow restrictor 48, and such a rapid filling will produce a more rapidly-delivered dosage to treatment area 38. Some embodiments may omit one-way check valve 49 if a more controlled dosage is desired. As a result of the compression of actuator 50, the piston associated with fluid reservoir 46, and correspondingly that of fluid reservoir 44, rises, drawing fluid through one-way check valve 40 into fluid reservoir 44. Upon deactuation, actuator 50 begins to expand and fill, drawing fluid through flow restrictor 48 from fluid reservoir 46. The rate at which the fluid is drawn is limited by the motivating forces of actuator 50, the viscosity of the fluid moving through flow restrictor 48, the size of flow restrictor 48, and any "hydraulic gearing" built into the system. This, in turn, affects the rate of the pharmaceutical solution flowing out of fluid reservoir 44 through one-way check valve 42 and to treatment area 38. As such, selecting restrictors, fluid viscosity, and hydraulic gearing allows for the selection of a supplemental flow rate. The volume of fluid moving from fluid reservoir 46 to actuator 50 dictates the duration of the supplemental flow rate or the total volume of the supplemental dosage. Consequently, the duration of supplemental fluid delivery may be adjusted by adjusting the volume of this working fluid that is associated with reservoir 46 and actuator 50. Hydraulic gearing refers to the relative volume of fluid moved in each of fluid reservoirs 44 and 46. The hydraulic gearing ratio can be set by incorporating a mechanism such that the stroke length traversed by the pistons is different for each chamber. The hydraulic gearing ratio could also be set by designing the chambers with different cross-sectional areas, such that even if the stroke length is the same, the volume expelled/aspirated is different. It is also possible to design chambers and gearing such that the gearing ratio is non-constant throughout the length of the stroke. This feature would be useful, for example, to compensate for an actuator pressure source that is not constant throughout its working range, or for example, to deliver a drug with a different dosage profile. Further, one-way check valves 40 and 42, in this exemplary embodiment, comprise an interlock system such that only one of check valves 40 or 42 allows fluid to pass at any given time.

Figure 2B:
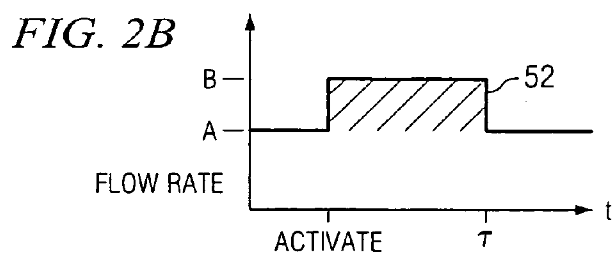

FIG. 2B depicts a chart of the flow rate of the pharmaceutical solution delivered to the treatment area 38. The solution is additionally delivered at a basal rate A until an actuation point. Upon actuation, the fluid reservoir 44 fills with fluid and gradually releases that fluid over a time (t). After the time (t), the system returns to the basal flow rate A. The volume 52 of fluid that is delivered as a supplemental dose is associated with the volume of fluid that is transferred between fluid reservoir 46 and actuator 50. The rate of delivery B and the total time (t) taken to deliver the supplemental dose of the pharmaceutical solution, are dictated, according to embodiments, by the restrictions and motivations associated with fluid flow back to actuator 50. Various restrictions and motivations may be used, such as a variable restrictor in place of flow restrictor 48, the selection of viscous fluids with varying viscosities, or the establishment of a motivating pressure within the actuator or spring force within the actuator.

The volume of fluid 52 delivered as a supplemental dose is associated with the volume transfer between fluid reservoir 46 and actuator 50. This association, according to embodiments of the invention, may be a ratio of one to one if the fluid reservoirs 44 and 46 are of the same size. However, the ratio may be varied by varying the size of the fluid reservoirs used according to embodiments or by using gearing to change the length of the stroke. In addition, the relationship may be linear if the cylinders are of the same shape or type. However, a non-linear relationship may be established between the flows with varying shaped cylinders or other membrane configurations.

In one exemplary embodiment, a physician may specify a desired supplemental prescription. The desired supplemental prescription may include a total dose over a given time or at a given rate. To implement the prescription, the physician may determine a volume of viscous working fluid to be placed in the actuator. In addition, the physician may select a restriction or motivation that provides the appropriate rate of fluid transfer. For example, the physician may select from a set of viscous working fluids with varying viscosities. Alternately, the physician may configure a restrictor or select from a set of varying restrictions. In a further example, the physician may select a spring force or pressure. However, various embodiments may be envisaged. In this manner, when actuator 50 is actuated, the corresponding supplemental dose may be specified by the physician and established in the device configuration. The method may be as simple as reading a chart or set of charts and injecting the appropriate volume of viscous working fluid into actuator 50.

Figure 3A:
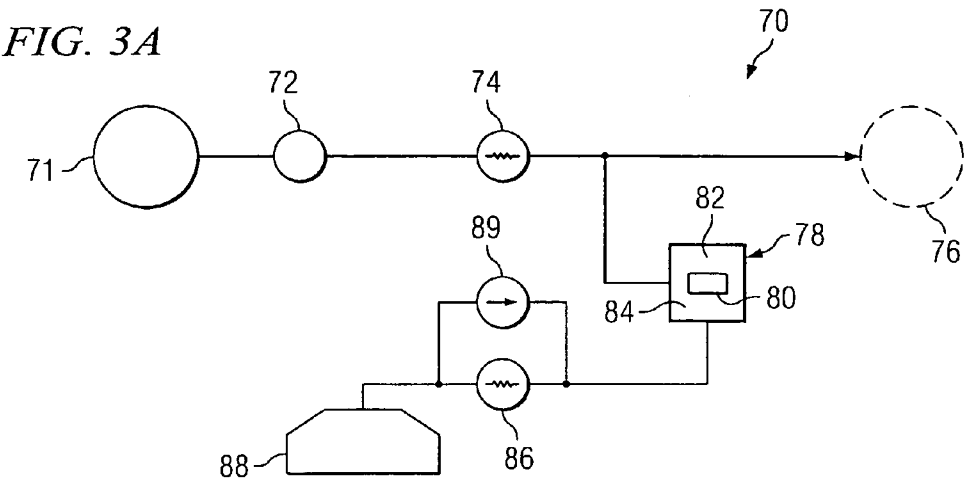
FIGS. 3A and 3C are schematic diagrams depicting other exemplary embodiments of the invention.
Figure 3B:
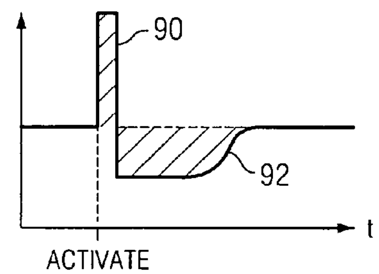
FIGS. 3B and 3D are graphs of dosage rates associated with the exemplary embodiments of FIGS. 3A and 3C, respectively.

FIG. 3A is a schematic diagram depicting another exemplary embodiment. System 70 includes reservoir 71 that motivates a pharmaceutical solution to travel through filter 72 and flow restrictor 74 to a treatment area 76. Actuator 88 may be activated to push fluid, such as working fluid having a selected viscosity, past flow restrictor 86 and into fluid reservoir 84 of piston system 78 of the illustrated embodiment. As fluid reservoir 84 fills with the viscous fluid, piston 80 is pushed against the fluid in fluid reservoir 82, pushing the fluid out into treatment area 76. This embodiment employs one-way check valve 89 to allow viscous fluid to bypass flow restrictor 86 on its way to fluid reservoir 84. Employing one-way check valve 89 facilitates a more rapid delivery of fluid into treatment area 76 than if the viscous fluid passed through flow restrictor 86. Alternative embodiments may omit one-way check valve 89 in order to produce a more controlled delivery of fluid to treatment area 76. Once deactuated, actuator 88 draws the viscous fluid from fluid reservoir 84 through flow restrictor 86. This, in turn, pulls piston 80 causing pharmaceutical agent to be drawn into fluid reservoir 82. The effect is seen in the chart shown in FIG. 3B.

Actuation causes a bolus dose of volume 90 to be introduced into the flow leading to the treatment area 76. Upon deactuation, the system draws fluid from the basal rate until the cylinder is refilled with a volume 92. In this example, the volumes 90 and 92 are equal. Thus, the total delivery dose over an extended period of time is unchanged. The only difference is that some drug is extracted, and some drug is delivered in a bolus flow rate.

With this configuration, repeated activation by a patient will not lead to an overdose as the amount of pharmaceutical agent in fluid reservoir 82 is limited by the amount of time over which fluid reservoir 82 draws fluid from the basal flow rate. As such, this configuration has a built-in safety feature, preventing overdosing caused by impatient or confused patients.

Figure 3C:
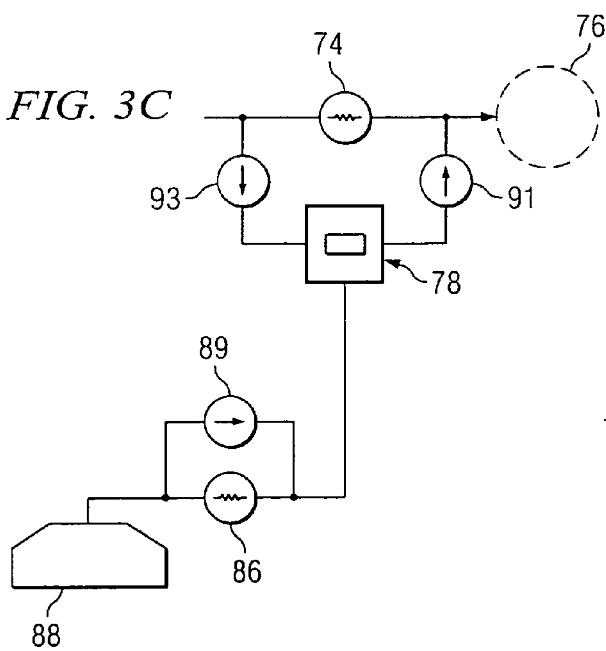
Figure 3D:
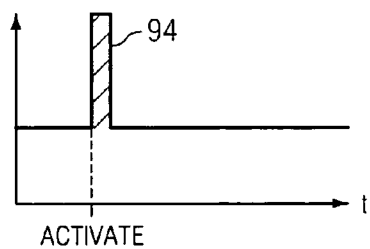

FIG. 3C depicts an alternate embodiment in which an actuator system, including actuator 88, flow restrictor 86 and piston system 78, are coupled to the flow system before flow restrictor 74. The system in this example embodiment employs one-way check valves 89, 91, and 93. One-way check valve 89 allows viscous fluid to bypass flow restrictor 86 on its way to piston system 78. One-way check valves 91 and 93 employ an interlock system such that only one of valves 91 or 93 will allow flow of viscous fluid at any one time. Actuation of such a system may produce a flow as seen in chart of FIG. 3D. In this exemplary embodiment, the bolus may be delivered as seen in a volume 94. However, over time, the patient may deliver multiple boluses that do not conform to the time-averaged basal fluid rate. Continuous manipulation of actuator 88 would asymptotically approach a time averaged fluid rate. After each actuation, the cylinder would only partially fill with solution, thus limiting the cumulative total dose over a given time period.

Figure 3E:
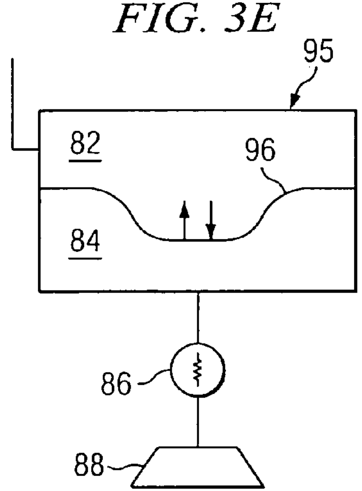
FIG. 3E is a schematic diagram depicting components of an exemplary embodiment of the invention.

FIG. 3E depicts and alternative embodiment in which fluid reservoirs 82 and 84 are implemented in rigid housing 95 and their respective volumes are defined by flexible membrane 96. Activation of actuator 88 results in an increase in a volume of fluid in reservoir 84 and a decrease in volume of fluid 82. Accordingly, deactuation of actuator 88 results in a decrease in volume of fluid in reservoir 84 and a corresponding increase in volume of fluid in reservoir 82. Among other possible applications, the embodiment illustrated in FIG. 3E may be implemented in the systems which are illustrated in FIGS. 3A and 3C, such as by replacing piston system 78 with rigid housing 95 and flexible membrane 96.

Figure 4A:
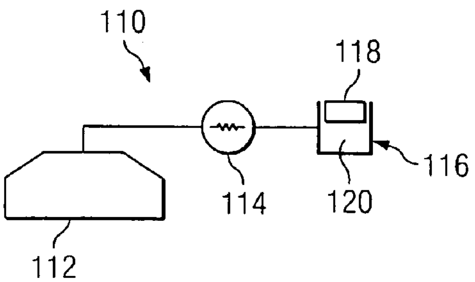
FIG. 4A is a schematic diagram depicting a further exemplary embodiment of the invention.

Example actuation system 110 is depicted in FIG. 4A. Actuator 112 is coupled to fluid reservoir 116 of the illustrated embodiment through flow restrictor 114. Actuation of actuator 112, either through mechanical or physical manipulation, pushes fluid through flow restrictor 114 and into fluid reservoir 120. Other embodiments may employ a one-way check valve similar to valve 89 in FIGS. 3A and 3C to allow fluid to bypass flow restrictor 114 in order to fill fluid reservoir 120 more quickly. As a result of filling fluid reservoir 120, piston 118 moves. Depending upon arrangements and couplings to piston 118, a subsequent reaction may be produced in the flow rate of the pharmaceutical solution, such as described in the above embodiment.

Once actuator 112 is deactuated, it draws fluid from fluid reservoir 120 through flow restrictor 114 at a rate dictated by the viscosity of the fluid, the size of flow restrictor 114, and the motivating force of actuator 112. Each of these elements may be manipulated to control the rate at which the piston moves and the time period over which the piston moves.

Figure 4B:
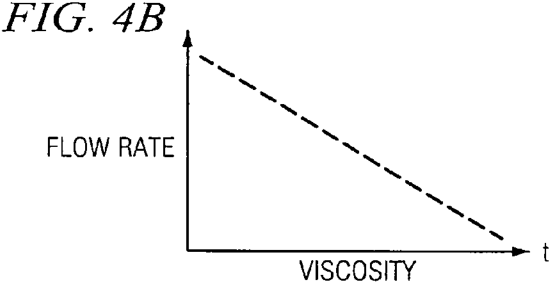
FIG. 4B is a graph of dosage rates associated with the exemplary embodiment of FIG. 4A.

For example, fluids having differing viscosities may change the rate at which piston 118 moves. As seen in FIG. 4B, low viscosity fluids would lead to a higher flow rate, while higher viscosity fluids would lead to a lower flow rate. However, this relationship need not be linear. In another example, flow restrictors may be interchanged to provide for more or less restriction. The greater the restriction or resistance to flow, the slower the flow rate. In another embodiment, a variable rate restrictor may be used and configured for a specified rate. In a further embodiment, the motivating force caused by the actuator for drawing a fluid may be manipulated. This manipulation may, for example, be the application of a back pressure or the tightening of a spring, among others. The greater the motivation force, the faster the rate.

Figure 5A:
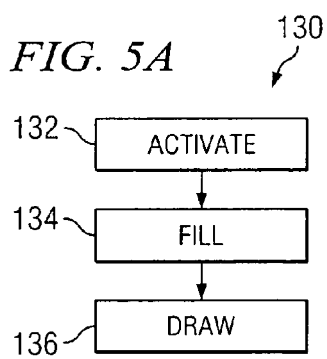
FIGS. 5A, 5B and 5C are block flow diagrams depicting an exemplary method for use of the invention.
Figure 5B:
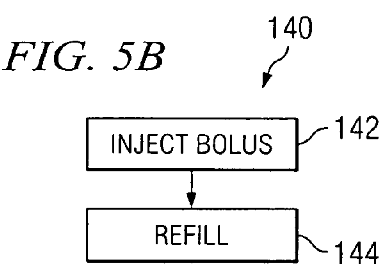
Figure 5C:
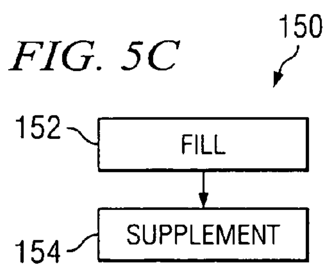

FIGS. 5A, 5B and 5C depict exemplary methods. FIG. 5A depicts method 130 for using the system as seen in FIG. 4A. The actuator may be actuated as seen in block 132. This actuation results in the filling of a chamber associated with a piston or moveable membrane as seen in block 134. The system may be configured such that the filling results in a bolus injection or the preparation for a supplemental dosage. Upon deactuation, fluid is drawn back into the actuator out of the chamber as seen in block 136. The drawing of fluids effectively reverses the direction of the piston or movement membrane causing a further reaction relative to the pharmaceutical solution.

For example, as seen in FIG. 5B, the method of FIG. 5A may result in the injection of a bolus dosage. Method 140 is illustrated in FIG. 5B, which depicts the injection of a bolus as seen in block 142, resulting in the filling of the chamber and movement of the piston or membrane. On deactuation and draw down of fluid out of the chamber, the bolus reservoir is refilled in block 144.

Embodiments may also be configured to provide a supplemental dosage. FIG. 5C depicts exemplary method 150. As a result of filling the chamber and activating the actuator, a supplemental reservoir or piston system is filled, as seen in block 152. As the actuator is deactuated and fluid is drawn out of the chamber, the system forces the pharmaceutical solution out of the supplemental reservoir and to the treatment area, as seen in block 154. However, embodiments may be configured in various ways to establish a variety of dosing schemes that result from the actuation and deactuation of the system.

Figure 6:
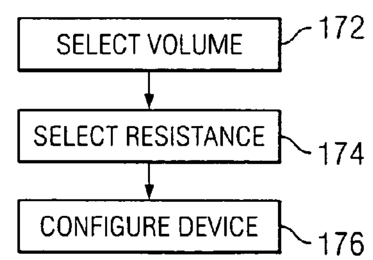
FIG. 6 is a block flow diagram depicting an exemplary method for use in implementing a prescription according to embodiments of the invention.

FIG. 6 depicts another exemplary method 170. To establish a prescription, physicians may determine a dosage rate for a first dosage and also may determine a second dosage. First, the doctor implements the first dosage as a basal flow dosage using a constant flow pump. A doctor may then implement the second dosage, as seen by the method 170. To begin implementing the second dosage, the doctor may select a volume of a viscous fluid to be moved by the actuator, as seen in block 172. Similarly, the doctor may select a resistance for the path of the viscous fluid, as seen in block 174. These in combination will determine the cumulative volume of the second dosage and the rate and time period over which the cumulative volume of the second dosage is delivered. The selection of resistance may take several forms, including selecting from varying liquids having various viscosities, selecting a restriction, employing a one-way check valve, and/or establishing a motivation force in the actuator.

Subsequently, as seen in block 176, the device may be configured with the constant flow pump and the selected resistance and volume. In this manner, the device will conform with the desired prescription and patients will be limited in their available dosage. However, patients will have a certain degree of control over their dosage schedule.

Subsequently, as seen in block 176, the device may be configured with the selected resistance and volume. In this manner, the device will conform with the desired prescription and patients will be limited in their available dosage. However, patients will have a certain degree of control over their dosage schedule.

As such, embodiments comprising systems and methods are described. In view of the above detailed description of the present invention and associated drawings, other modifications and variations will now become apparent to those skilled in the art. It should also be apparent that such other modifications and variations may be effected without departing from the spirit and scope of the present invention.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of operating an implantable infusion drug pump, comprising:

storing infusate in a main reservoir of the implantable infusion drug pump, wherein a substantially constant fluid pressure is provided to the infusate in the main reservoir;

driving infusate from the main reservoir through a flow restrictor and out through a discharge port of the implantable infusion drug pump at a substantially constant basal infusion rate;

providing a temporary bolus infusion rate in response to patient manipulation of provided simultaneously to the basal infusion rate, wherein the providing a temporary bolus infusion rate comprises: (i) driving fluid into a working fluid reservoir by pressure applied by the actuator, the working fluid reservoir and a secondary reservoir being mechanically coupled, the driving of fluid into the working fluid reservoir causing infusate to be drawn from the main reservoir into the secondary reservoir; (ii) providing pressure on infusate in the secondary reservoir to drive the infusate from the secondary reservoir, driving of infusate from the secondary reservoir occurring simultaneously with fluid being driven from the working fluid reservoir toward the actuator; and (iii) controlling a discharge rate from the secondary reservoir to the discharge port using a flow restrictor;

wherein the implantable infusion drug pump does not comprise an electrical motor or an electrical power supply;

wherein the implantable infusion drug pump comprises at least one one-way valve that enables the secondary reservoir to be filled without being subjected to a flow rate limitation of a flow restrictor of the implantable drug infusion pump.

2. The method of claim 1 wherein the secondary and working fluid reservoirs are defined by respective piston cylinders.

3. The method of 1 wherein the secondary reservoir is adapted to hold a maximum fluid volume that is greater than a maximum fluid volume of the working fluid reservoir.

4. The method of claim 1 wherein the driving infusate from the main reservoir is performed by an elastomeric diaphragm.

* * * * *

UNITED STATES PATENT AND TRADEMARK OFFICE

CERTIFICATE OF CORRECTION

PATENT NO. : 7,559,926 B1
APPLICATION NO. : 10/755985
DATED : July 14, 2009
INVENTOR(S) : Brian Blischak It is certified that error appears in the above-identified patent and that said Letters Patent is hereby corrected as shown below:

Column 10, line 6, "of provided" should read --of an actuator of the implantable infusion drug pump, wherein the bolus infusion rate is provided--.

Signed and Sealed this

Eighth Day of September, 2009

David J. Kappos

*Director of the United States Patent and Trademark Office*